United States Patent
Scherner et al.

(10) Patent No.: US 10,617,630 B2
(45) Date of Patent: Apr. 14, 2020

(54) EMULSIFIER-FREE, SKIN CONDITIONING AND ACTIVE INGREDIENT-CONTAINING COSMETIC OR DERMATOLOGICAL PREPARATION

(71) Applicant: BEIERSDORF AG, Hamburg (DE)

(72) Inventors: Cathrin Scherner, Norderstedt (DE); Inken Groth, Hamburg (DE); Magdalena Von Wedel-Parlow, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 371 days.

(21) Appl. No.: 14/914,838

(22) PCT Filed: Aug. 25, 2014

(86) PCT No.: PCT/EP2014/067974
§ 371 (c)(1),
(2) Date: Feb. 26, 2016

(87) PCT Pub. No.: WO2015/028417
PCT Pub. Date: Mar. 5, 2015

(65) Prior Publication Data
US 2016/0220475 A1 Aug. 4, 2016

(30) Foreign Application Priority Data

Aug. 29, 2013 (DE) .......... 10 2013 217 244
Feb. 19, 2014 (DE) .......... 20 2014 001 438 U
Feb. 24, 2014 (DE) .......... 20 2014 001 570 U

(51) Int. Cl.
| | |
|---|---|
| *A61K 8/81* | (2006.01) |
| *A61K 8/92* | (2006.01) |
| *A61Q 19/02* | (2006.01) |
| *A61Q 19/04* | (2006.01) |
| *A61K 8/31* | (2006.01) |
| *A61K 8/34* | (2006.01) |
| *A61Q 19/10* | (2006.01) |
| *A61K 8/35* | (2006.01) |
| *A61K 8/66* | (2006.01) |
| *A61K 8/87* | (2006.01) |
| *A61K 8/89* | (2006.01) |
| *A61Q 19/00* | (2006.01) |

(52) U.S. Cl.
CPC ............ *A61K 8/927* (2013.01); *A61K 8/31* (2013.01); *A61K 8/34* (2013.01); *A61K 8/342* (2013.01); *A61K 8/345* (2013.01); *A61K 8/355* (2013.01); *A61K 8/66* (2013.01); *A61K 8/81* (2013.01); *A61K 8/8141* (2013.01); *A61K 8/8147* (2013.01); *A61K 8/8152* (2013.01); *A61K 8/87* (2013.01); *A61K 8/89* (2013.01); *A61K 8/92* (2013.01); *A61K 8/922* (2013.01); *A61Q 19/00* (2013.01); *A61Q 19/004* (2013.01); *A61Q 19/02* (2013.01); *A61Q 19/04* (2013.01); *A61Q 19/10* (2013.01); *A61K 2800/30* (2013.01); *A61K 2800/33* (2013.01)

(58) Field of Classification Search
CPC ..... A61K 8/8141; A61K 8/8147; A61K 8/922
See application file for complete search history.

(56) References Cited

U.S. PATENT DOCUMENTS

| | | | | |
|---|---|---|---|---|
| 5,707,612 A | * | 1/1998 | Zofchak | ......... A61K 8/87 424/61 |
| 7,368,122 B1 | | 5/2008 | Dow et al. | |
| 7,977,289 B2 | * | 7/2011 | Patel | ......... A61K 8/06 424/70.1 |
| 2006/0239953 A1 | * | 10/2006 | Clapp | ......... A61K 8/31 424/70.22 |
| 2007/0025940 A1 | * | 2/2007 | Robert | ......... A61K 8/361 424/64 |
| 2010/0322876 A1 | * | 12/2010 | Nguyen | ......... A61K 8/645 424/59 |
| 2011/0071223 A1 | | 3/2011 | Ishii et al. | |
| 2012/0302760 A1 | | 11/2012 | Preschel et al. | |
| 2013/0108572 A1 | | 5/2013 | Balcke et al. | |
| 2013/0142737 A1 | | 6/2013 | Schlifkeposchalko et al. | |
| 2014/0030198 A1 | | 1/2014 | Fares et al. | |

FOREIGN PATENT DOCUMENTS

| | | |
|---|---|---|
| EP | 2153814 A1 | 2/2010 |
| NO | 2012149355 | 11/2012 |
| WO | 2013064391 | 5/2013 |

* cited by examiner

*Primary Examiner* — Lakshmi S Channavajjala
(74) *Attorney, Agent, or Firm* — Abel Schillinger, LLP

(57) ABSTRACT

The invention relates to an emulsifier-free, skin conditioning cosmetic or dermatological preparation which contains active ingredients.

1 Claim, No Drawings

EMULSIFIER-FREE, SKIN CONDITIONING AND ACTIVE INGREDIENT-CONTAINING COSMETIC OR DERMATOLOGICAL PREPARATION

BACKGROUND OF THE INVENTION

1. Field of the Invention

The invention comprises an emulsifier-free, skin conditioning cosmetic or dermatological preparation with active ingredients. The preparation is suitable for application to wet skin without being completely rinsed off and thereby allows for rubbing in during showering and the application of skincare and/or skin-protecting active ingredients.

2. Discussion of Background Information

Rubbing in under wet conditions, skincare in the shower, is understood in summary as skin conditioning. This means inter
1. use of a customary shower product for cleaning the skin, rinsing off
2. application/spreading of the preparation according to the invention on wet skin
3. renewed showering off with warm or cold water
4. drying off of the skin.

WO 2013064391 A2 describes cosmetic or dermatological preparations which allow rubbing in under the shower.

On account of a lack of time, many people desire the most efficient possible skincare and simultaneous skin protection.

It is desirable to provide a preparation which, on the one hand, is designed to be skin-compatible and, on the other hand, opens up the possibility of applying skincare and/or skin-protecting active ingredients to the skin and can therefore be applied in a time-saving manner under the shower and/or to wet skin.

SUMMARY OF THE INVENTION

The invention is an emulsifier-free cosmetic or dermatological preparation comprising one or more polyacrylic acid polymers, one or more C14-22 fatty alcohols, and one or more waxes and/or a hydrocarbon mixture, and one or more active ingredients.

Preferably, the preparation comprises waxes, in particular Cera Microcristallina, in the region of more than 0.5% by weight, in particular more than 13% by weight, based on the total mass of the preparation.

The preferred fraction refers both to the individual waxes and also preferably to the total amount of several waxes.

The active ingredients according to the invention encompassed are all cosmetically or dermatologically acting substances, in particular those substances which have a skincare and/or skin-protecting property.

The active ingredients can preferably be selected from the group of skincare substances, self-tanning agents, cooling substances, warming substances and/or whitening (skin-lightening) substances. Preference is given in each case to selecting one or more active ingredients from only one of the aforementioned groups.

The skincare substances to be selected are advantageously those substances which make the skin soft and have a smoothing effect, i.e. reduce roughness, as are active ingredients which keep the skin in a healthy condition, avoid harmful effects on the skin due to external influences and/or moisturize.

Active ingredients that can be selected are one or more from the group of cyclodextrin, ubiquinone, creatine, 1-methylhydantoin-2-imide, glycine soya germ extract, ascorbic acid (vitamin C and derivatives thereof), ascorbyl palmitate, sodium ascorbyl phosphate, *Pimpinella Anisum* fruit extract, *Arctium Lappa* fruit extract, *Magnolia Officinalis* bark extract, sodium hyaluronate, taurine, folic acid, *Glycyrrhiza Inflata* root extract, glycyrrhetinic acid, glucosylrutin and isoquercitrin, carnitine, sodium chloride, glyceryl glucoside, climbazole, piroctone olamine, oryzanol, BHT, tocopherol, vitamins, in particular vitamin E and A and derivatives thereof, tocopheryl acetate, *Nelumbo Nucifera* leaf extract, caffeine, *Camellia Sinensis* leaf extract, menthoxypropanediol, menthane carboxamide ethylpyridine, cyanomethyl phenyl menthane carboxamide, *Chelidonium Majus* extract, salicylic acid, 4-butylresorcinol, *Paullinia Cupana* seed extract, butyl acrylate/ethyltrimonium chloride, methacrylate/styrene copolymer, octenidine HCl, urea, octadecenedioic acid, dihydroxyacetone, cholesterol, ceramide 3, silver citrate, arginine HCL, *Fucus Vesiculosus* extract, panthenol, niacinamide (vitamin B3), retinyl palmitate/retinol, biotin, bisabolol, menthol, alanine, allantoin, *Pyrus Malus* stem extract, acetyl hydroxyproline, *Laminaria Ochroleuca* extract, zingerone, 4-t-butylcyclohexanol, *Garcinia Cambogia* fruit extract, epsilon-polylysine, raspberry ketone, alexidine, N-(4-(2,4-dihydroxyphenyl)thiazol-2-yl) isobutyramide, dihydromyricetin, silymarin, 3-(4-hydroxy-3-methoxyphenyl)-1-(4-hydroxyphenyl)propan-1-one, pyridoxine-3,4-cyclic phosphate, oxygen, dioic acid, glyceryl glucose.

Preferred active ingredients to be selected are D-biotin, coenzyme Q10, folic acid and/or derivatives thereof, rucinol, panthenol, niacinamide, alpha-glucosylrutin, carnitine, carnosine, natural and/or synthetic isoflavonoids, creatine, taurine, β-alanine, 1-methylhydantoin-2-imide, N-(4-(2,4-dihydroxyphenyl)thiazol-2-yl) isobutyramide, glycine soya germ extract, *Pimpinella Anisum* fruit extract, *Arctium Lappa* fruit extract, *Magnolia Officinalis* bark extract, sodium hyaluronate, *Glycyrrhiza Inflata* root extract, glycyrrhetinic acid, glucosylrutin and isoquercitrin, sodium chloride, glyceryl glucoside, climbazole, piroctone olamine, menthoxypropanediol, menthane carboxamide ethylpyridine, cyanomethyl phenyl menthane carboxamide and/or 4-butylresorcinol.

In particular, the active ingredient to be selected is Q10.

The self-tanning agents used advantageously according to the invention are, inter alia:

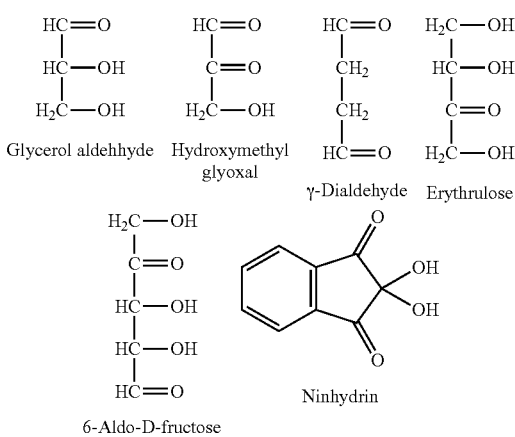

Furthermore, mention is to be made of 5-hydroxy-1,4-naphthoquinone (juglone), which is extracted from the shells of fresh walnuts

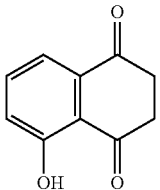

5-Hydroxy-1,4-naphthoquinone (juglone)

as well as 2-hydroxy-1,4-naphthoquinone (lawsone), which occurs in henna leaves.

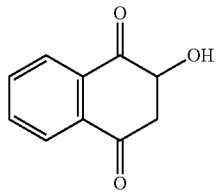

2-Hydroxy-1,4-naphthoquinone (lawsone).

In the context of the invention, very particular preference is given to 1,3-dihydroxyacetone (MIA), a trivalent sugar that occurs in the human body.

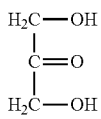

1,3-Dihydroxyacetone (DHA)

The use of self-tanning substances as active ingredients in the preparation according to the invention permits a time-saving application and the entire body can thus be tanned without problem for the first time.

As warming substances, substances that stimulate the circulation, such as capsaicinoids, are known as active ingredients. The mode of action of these products is based firstly on the promotion of circulation in the areas affected and secondly on an influence on the metabolism. Thus, for example, capsaicin stimulates the elimination of substance P, a neuropeptide made of eleven amino acids. This molecule actively interferes in the pain cycle and contributes to reducing the perceived pain.

The circulation-promoting active ingredients used are preferably

| |
|---|
| Capsaicinoids (0.01-0.20%) |
| Nonivamide (0.01-0.15%) |
| Vanilyl butyl ether (0.5-2.5%) |
| Nicotinic acid benzyl ester (0.5-4.0%) |
| Rosemary oil (0.5-5.0%) |
| Capsiate (vanilli acid ester) (0.5-2.5%) |
| Mustard oils (0.2-4.0%) |

Further active ingredients to be used according to the invention are to be selected from the group of non-warming, anti-inflammatory active ingredients from the area of non-steroidal anti-inflammatory drugs (NSAIDs). In particular, these are aspirin (acetylsalicylic acid), diflunisal, salsalate, ibuprofen, etofenamate, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, licofelone, lysine clonixinate, hyperforin and/or figwort. Preference is given here to ibuprofen, diclofenac and salts thereof, indomethacin, flurbiprofen and etofenamate.

Particular preference is given to the incorporation of one or more substances which are known for their long-lasting cooling properties, e.g. menthol and derivatives thereof, camphor, mint, *eucalyptus* etc.

A particularly preferred essential oil has proven to be menthol. Menthol is a constituent of the known Japanese peppermint oil (CAS: 20747-49-3). The most important isomer is (−)-menthol. Upon rubbing on the skin, menthol produces a pleasant cool feel as a result of surface anesthetization and stimulation of the cold-sensitive nerves in the case of migraines or the like. As has been proven, however, the affected areas of skin exhibit normal or increased temperature.

Further preferred essential oils that can be used are Oleum Eucalypti, Oleum Menthae Piperitae, Oleum Camphoratum, Oleum Rosmarini, Oleum Thymi, Oleum Pini Sibricum and Oleum Pini Silverstris, and the terpenes 1,8-cineol and levomethanol, and also Oleum Abietis Albae, Oleum Anisi, Oleum Aurantii Oleum Bergamottae, Oleum Calendulae Infusum, Oleum Caryophylli, Oleum Chamomillae, Oleum Cinnamomi Ceylanici, Oleum Citri, Oleum Citronellae, Oleum Cupressi, Oleum Cymbopogonis, Oleum Jecoris, Oleum Lavendulae, Oleum Macidis, Oleum Majoranae, Oleum Melaleucae Viridiflorae, Oleum Melissae, Oleum Menthae Arvensis, Oleum Millefolium, Oleum Myrrhae, Oleum Myrte, Oleum Pini Sibricum, Oleum Pinisilvestris, Oleum Salviae, Oleum Santali, Oleum Terebinthinae Rectificat, Oleum Valerianae and Oleum Zingiberis.

The essential oils are used individually or in combination with others to a fraction of in total 0.001 to 10% by weight, in particular to 0.01 to 1% by weight, in the preparation, based on the total mass of the preparation without propellants.

Advantageously, instead of the seemingly cooling acting substances, it is also possible to use substances which are known for warming properties, such as, for example, HotAct (vanillyl butyl ether) and/or *capsicum*.

Whitening substances are substances for lightening the skin. This is understood as meaning the bleaching or coating of the human skin in order to make it lighter for cosmetic purposes.

Preferred whitening substances are rucinol, hydroquinones, kojic acid, liquorice root extract, N-(4-(2,4-dihydroxyphenyl)thiazol-2-yl)isobutyramide, camu camu, liquorice, acerola or vitamin C.

A distinction is made between tyrosinase inhibitors and melanin synthesis inhibitors since the inhibition of the tyrosinase results in the inhibition of the melanin synthesis, but the inhibition of the melanin synthesis does not automatically mean tyrosinase inhibition.

Rucinol, hydroquinones and kojic acid for example also inhibit the tyrosinase.

The use concentration in weight fractions of one or more of the active ingredients in the applied preparation is preferably up to 25% by weight, in particular in the range between 0.001% by weight and 20% by weight, based on the total mass of the preparation.

According to the invention, the selection of the active ingredients is advantageously to be selected from the group of lipophilic compounds.

Since the basic preparation according to the invention is composed of predominantly lipophilic substances, a longer stay on the skin can thus be realized.

Preferably, the preparation according to the invention comprises Q10 and menthol as active ingredients.

Besides a cooling effect during and after showering, skincare effects are achieved at the same time.

Surprisingly, active ingredients remain on the skin after washing and drying through the preparation according to the invention. The application of the combination of specific fatty alcohols, waxes and advantageously one or more film formers leads to skin protection and/or skincare even while showering.

The preparations according to the invention advantageously comprise one or more film formers.

These film formers are advantageously selected from the group hexadecene copolymer, trimethylsiloxysilicate, polypropylsilsesquioxane, polysilicone-25, acrylate copolymer, polyurethane, methacrylate, polyglyceryl stearate, dilinoleate crosspolymer, alkyl acrylate/methacrylic acid crosspolymer, IPDI copolymer, in particular VP/hexadecene copolymer, octyldodecyl citrate crosspolymer, trimethylsiloxysilicate/polypropylsilsesquioxane, polysilicone-25, ammonium acrylate copolymer, acrylate copolymer, polyurethane-2 and polymethyl methacrylate, polyglyceryl stearate/isostearate dilinoleate crosspolymer, octadecene/MA copolymer (and) methyl acetyl ricinoleate (and) diisooctyl adipate, trimethylsiloxysilicate, polyurethane-34, C8-22 alkyl acrylate/methacrylic acid crosspolymer and/or castor oil/IPDI copolymer.

The fraction of film formers is advantageously selected in the region of 0.1% by weight, in particular 0.5% by weight to 10% by weight, based on the total mass of the preparation.

In a comparison, the protective film that foil is on the skin is investigated, once following the application of a rinse-off product with integrated skincare aspects (Nivea créme soft shower gel) on its own and once following application of the same product (Nivea créme soft shower gel) and subsequent application of the preparation according to the invention. After both applications, the skin is rinsed with water.

The measurements carried out with regard to refitting of the skin were made by IR imaging. The measurement technique is called IR-ATR (InfraRed-Attenuated Total Reflectance).

It was found that a protective film, visible by means of the mentioned measurement technique, remains on the skin and is detectable only following application of the preparation according to the invention. The demonstration takes place via the intensity of the hydrocarbon-IR bands (CH-IR bands).

The protective film according to the invention comprises a film which is formed on the skin and comprises one or more active ingredients. Lipophilic active ingredients are to be selected advantageously as they remain for longer in the film and therefore on the skin.

The skin conditioning according to the invention comprises the rubbing in under wet conditions, in particular skincare while showering, where a protective film also remains on the skin after rinsing. The protective film can be detected by means of IR-ATR measurement technique and ideally has a thickness of at least 1 μm to 10 μm.

In particular, the skin conditioning according to the invention is characterized in that one or more active ingredients, one or more lipids and one or more skin-wetting agents are comprised and none of the substances that damage the skin barrier, in particular no emulsifiers and/or surfactants, are present in the protective film on the skin.

Only this film remaining on the skin permits the application and also the retention of active ingredients on the skin.

In the preparation according to the invention, one or more fatty alcohols and at least one additional wax and/or mixture of liquid and solid hydrocarbons, with a melting range from 5° C. to 75° C., preferably up to 55° C. (according to DSC), are combined, in particular melted.

I.e., advantageously, besides at least one fatty alcohol, at least one wax is present or besides fatty alcohol, at least one mixture of liquid and solid hydrocarbons is present. Ideally, fatty alcohol, wax and a mixture of hydrocarbons are present.

Advantageously, fatty alcohols to be selected are myristyl, cetearyl and/or stearyl alcohols, the waxes are Cera Microcristallina, coco glyceride, C18-36 acid triglyceride, synthetic wax, Cera Alba, paraffin, *Copernicia Cerifera* Cera, C18-38 alkyl hydroxystearoylstearate, *Butyrospermum Parkii* butter, olus oil, C20-40 alcohol and/or beeswax, and the hydrocarbon mixture is Paraffinum Liquidum. Preference is given to Cera Microcristallina.

Preferred use concentrations of the wax or waxes is in the range from 0.5 to 20% by weight, based on the total mass of the preparation.

The fatty alcohols, waxes and hydrocarbon mixtures here all advantageously have a melting range from 5° C. to 75° C., preferably up to 55° C. (according to DSC).

DSC (differential scanning calorimetry) is a thermal method for measuring the amount of heat released/taken up by a sample during an isothermal procedure, heating or cooling (see DIN 53765, DIN 51007, ASTM E 474, ASTM D 3418). DSC is a comparative measurement method which permits the determination of amounts of heat of physical and chemical processes. If a material changes its physical state, such as e.g. melting or conversion of one crystalline form into another or if it reacts chemically, heat is taken up or released in the process. These amounts of heat can be measured quantitatively with the help of DSC. The method proceeds cyclically, such that, after the first heating curve, a defined cooling takes place and then the sample is heated once again in the given temperature range. Two kinds of information are thus obtained: in the first heating curve, all thermal effects including past history are evident. In the second heating curve, the past history has been eliminated and the pure thermal behavior of the sample can be evaluated under defined cooling conditions. The melting range of the fatty alcohols, waxes and hydrocarbons of between 4.5° C. and 75° C. according to DSC is the range determined in the first heating curve.

According to the invention, waxes that can be used are also fats and fat-like substances with a wax-like consistency. These include, inter alia, fats (triglycerides), mono- and diglycerides, natural and synthetic waxes, fat and wax alcohols, esters of fatty alcohols and fatty acids, and also fatty acid amides or any desired mixtures of this substance.

Particularly preferably, the waxes are selected from the group of fats, in particular from the group of natural waxes: *Shorea Stenoptera* seed butter, hydrogenated vegetable oil, hydrogenated coco glycerides, *Butyrospermum Parkii* butter, *Theobroma Cacao* (cocoa) seed butter, mango butter, hydrogenated palm kernel glycerides, hydrogenated palm glycerides, sunflower seed wax, soybean glycerides, *Butyrospermum Parkii* Unsaponifiables, wool wax, Cera Alba, beeswax, sugar cane wax, Cera Carnauba, candelilla wax, Japan wax, hydrogenated rapeseed oil, shellac wax, hydrogenated lecithin, hydrogenated soybean oil, from the group of synthetic waxes, in particular from:
Cera Microcristallina, synthetic beeswax, synthetic wax, polyethylene, paraffin wax, ceresin, ozokerite, from the group of fatty acids, in particular from:
palmitic acid, stearic acid, from the group of esters of fatty acids, in particular from:
cetearyl nonanoate, methyl palmitate, glyceryl tribehenate, glyceryl laurate, glyceryl stearate, cetyl palmitate; shea butter oleyl esters, PEG-8 beeswax.

Preferred additives are also *Butyrospermum Parkii* butter, *Cocos Nucifera* oil, and/or *Cananga Odorate* Flower oil.

The fatty alcohols used are preferably C14 to C22 fatty alcohols. Preferably, the fatty alcohols are selected from the group of linear fatty alcohols, in particular myristyl alcohol ($C_{14}H_{30}O$), cetyl alcohol (or palmityl alcohol) ($C_{16}H_{34}O$), stearyl alcohol (or octadecyl alcohol) ($C_{18}H_{38}O$), and cetylstearyl alcohol (cetearyl alcohol), behenyl alcohol, lanolin alcohol, a mixture of the alcohols cetyl alcohol (hexadecanol) and stearyl alcohol (octadecanol).

The fraction of C14-22 fatty alcohols overall is advantageously 0.5 to 14% by weight, in particular 7 to 9% by weight, or in particular 0.5-5%, based on the total mass of the preparation.

The hydrocarbon mixtures used are preferably hydrocarbon gels or mixtures of liquid and solid paraffin hydrocarbons. Preferably, the content of solid hydrocarbons in the hydrocarbon mixture is between 1 and 50%, particularly preferably between 10 and 30%. The use of hydrocarbon mixtures which form fringed micelles or paracrystalline structures is advantageous.

The fraction of the hydrocarbon mixture overall is advantageously 1 to 50% by weight, in particular 20 to 30% by weight, based on the total mass of the preparation.

According to the invention, fatty alcohol, in particular two or three fatty alcohols, are obligatorily present in the preparation. Additionally, one or more waxes are added to the preparation. Preferably, instead of the wax, it is also possible to add a hydrocarbon mixture of hydrocarbons that are liquid and solid at room temperature.

Ideally, the preparation comprises all three building blocks, fatty alcohols, waxes and hydrocarbon mixture.

Cosmetic or dermatological substances known to the person skilled in the art can then be added to the production and preparation according to the invention, in which case their addition must not adversely affect the skin-conditioning properties of the obtainable preparation.

Thickeners, fillers and neutralizing agents are advantageously added to the preparations.

Thickeners are advantageously suitable for stabilizing the system and boost the skin-conditioning properties and the special skin feel of the preparations according to the invention.

The filler added is preferably aluminum starch octenylsuccinate, which likewise leads to an optimization of the skin feel in that the skin protective film acts somewhat more velvety.

The neutralizing agent added is advantageously sodium hydroxide solution, so that the thickeners can form their gel network and a stable system is formed.

The preparation according to the invention is emulsifier-free, i.e., in accordance with the invention, the polyacrylic acid polymers which may have an emulsifying effect are not taken to be emulsifiers.

In other words, besides the polyacrylic acid polymers, no further emulsifiers are added to the preparation.

Emulsifier-free also encompasses a minimum content of additional emulsifiers of less than 1% by weight, based on the total mass of the preparation, which may be present, for example, as a result of contaminations or entrainments. The influence on the product performance in these quantitative ranges is insignificant if appropriate.

However, preference is given to a content of emulsifiers of 0% by weight.

The polyacrylic acid polymers are understood as being the polymers of acrylic acid and/or methacrylic acid, and acrylate crosspolymers known in cosmetics.

Preferably, these are polymers (macromolecules) with a high molecular weight (>1 mg/mol) which consist of a backbone of polyacrylic acid and small amounts of polyalkenyl ether crosslinkages. They are also referred to as carbomers. These water-soluble or dispersible polymers can bring about a significant increase in viscosity in the liquid in which they are dissolved or dispersed. This is brought about by the formation of carbomer microgels in the water.

Besides the carbomers, particularly preferred polyacrylic acid polymers are those acrylate crosspolymers which exert a polymeric emulsifier effect.

Polymeric emulsifiers are primarily polyacrylic acid polymers with a high molecular weight. These emulsifying polyacrylic acid polymers have a small lipophilic fraction in addition to the hydrophilic main part. In the context of the present invention, very particular preference is given to acrylate crosspolymers which have the INCI name "Acrylates/C10-30 Alkyl Acrylate Crosspolymer" and are obtainable under the trade names Pemulen TR-1 and Pemulen TR-2, and also Carbopol 1342, Carbopol 1382 and Carbopol ETD 2020 from NOVEON.

The polyacrylic acid polymers are particularly preferably selected from the group of acrylates/C10-30 alkyl acrylate crosspolymers and/or carbomers. Particular preference is given to acrylates/C10-30 alkyl acrylate crosspolymer Pemulen® TR-1, e.g. from Lubrizol and Carbopol® 3128 from Lubrizol.

A specific combination of polyacrylic acid polymers with an emulsifying effect, such as the Pemulen TR-1 with other polyacrylic acid polymers, such as Carbopol 3128, which improve the sensory properties and ensure the stability of the preparation, especially at higher temperatures, and a compound with free water is in accordance with the invention here.

Particular preference here is given to a combination of three polyacrylic acid polymers, where one polyacrylic acid polymer has an emulsifying effect, such as e.g. the Pemulen TR-1 or Pemulen TR-2, with other polyacrylic acid polymers which improve the sensory properties and ensure the stability of the preparation, especially at higher temperatures (e.g. Carbopol 3128) and a polyacrylic acid polymer which improve the sensory properties upon absorption of free water (e.g. Carbopol 981).

The preparation according to the invention advantageously therefore comprises preferably at least three polyacrylic acid polymers, in particular three polyacrylic acid polymers which differ in their properties.

The fraction of polyacrylic acid polymers overall is preferably 0.05 to 2% by weight, in particular 0.2 to 1% by weight, based on the total mass of the preparation.

The combination of at least two polyacrylic acid polymers with at least two C14-22 fatty alcohols has proven to be advantageous for the improved stabilization of the preparation and in particular the skin feel when used on damp/wet skin is not unpleasant, nonwaxy, harsh or squeaky.

According to the invention, two polyacrylic acid polymers or three polyacrylic acid polymers are to be understood such that in each case one polyacrylic acid polymer differs from the others in each case in at least one property. The substance group acrylates/C10-30 alkyl acrylate crosspolymers includes, for example, the commercial products Pemulen TR-1 and TR-2.

Carbomers differ for example in types A, B and C. Differences are herein for example their gels with different viscosities (United States Pharmacopoeia, USP).

Moreover, a fraction of waxes or preferably a mixture of liquid and solid hydrocarbons with a melting range from 4.5 to 75° C., in particular up to 55° C. according to DSC is essential to the invention and therefore preferred.

Nonpolar to medium-polar lipids can optionally advantageously be added as oils to the preparations according to the invention. Otherwise, the stability is more difficult to establish on account of the freedom from emulsifiers.

In the context of the present disclosure, the generic term used for fats, oils, waxes and the like is the expression "lipids", as is entirely familiar to the person skilled in the art. The terms "oil phase" and "lipid phase" are also used synonymously.

Oils and fats differ inter alia in their polarity. It is proposed to adopt the interfacial tension towards water as a measure of the polarity index of an oil or of an oil phase. This means that the polarity of the oil phase in question is greater, the lower the interfacial tension between this oil phase and water is. According to the invention, the interfacial tension is considered to be a possible measure of the polarity of a given oil component.

The interfacial tension is any force which acts on an imaginary line, one meter in length, in the interface between two phases. The physical unit for this interfacial tension is classically calculated according to the force/length relationship and is usually given in mN/m (millinewtons divided by meters). It has a positive sign if it endeavors to make the interface smaller. In the reversed case, it has a negative sign.

The preparation according to the invention permits for the first time the application of care while showering, and also the application of active ingredients even during the showering process.

The preparations according to the invention are advantageously only formulated with preservatives which have a solubility in water of more than 0.75% at 20° C. On account of the lack of emulsifiers, destabilizations and crystallization may otherwise result.

The preparations according to the invention are furthermore preferably also free from surfactants.

Surfactants are substances which reduce the surface tension of a liquid or the interfacial tension between two phases and permit or assist the formation of dispersions. Surfactants enable two liquids that are actually immiscible with one another, such as, for example, oil and water, to be dispersed.

Furthermore, surfactants are described as amphiphilic substances which are able to dissolve organic, nonpolar substances in water. As a consequence of their specific molecular structure with at least one hydrophilic and one hydrophobic molecular moiety, they provide for a reduction in the surface tension of the water, the wetting of the skin, the facilitation of soil removal and dissolution, easy rinsing off and—according to desires—foam regulation.

The hydrophilic moieties of a surfactant molecule are mostly polar functional groups, for example $—COO^-$, $—OSO_3^{2-}$, $—SO_3^-$, whereas the hydrophobic moieties are generally nonpolar hydrocarbon radicals. Surfactants are generally classified according to type and charge of the hydrophilic molecular moiety. In this connection, four groups can be differentiated:
 anionic surfactants,
 cationic surfactants,
 amphoteric surfactants and
 nonionic surfactants.

Anionic surfactants generally have carboxylate, sulfate or sulfonate groups as functional groups. In aqueous solution, they form negatively charged organic ions in an acidic or neutral medium. Cationic surfactants are characterized virtually exclusively by the presence of a quaternary ammonium group. In aqueous solution, they form positively charged organic ions in the acidic or neutral medium. Amphoteric surfactants contain both anionic and cationic groups and behave accordingly in aqueous solution as anionic or cationic surfactants depending on the pH. In a strongly acidic medium, they have a positive charge and in an alkaline medium, a negative charge.

Furthermore, detersive substances are known, such as, for example, cationic surfactants, in particular quaternary ammonium compounds. A detersive substance is used in detergents, washing up compositions, shampoos, shower gels and refers to the fraction of the formulation which influences the washing or cleaning performance. Detersive substances increase the "solubility" of fat and grease particles in water which adhere in the laundry or on the body. They can be of natural or synthetic origin. They are divided according to their type of charge into anionic, cationic, amopholytic or nonionic.

Emulsifiers enable two liquids that are immiscible with one another (for example oil in water) to combine to give an emulsion. On account of the amphiphilic character, they penetrate into the oil with their fat-soluble moiety. As a result of the hydrophilic moiety, the oil droplet produced by stirring can then be dispersed in the aqueous environment. Emulsifiers primarily have no washing active surfactant character.

Emulsifiers and surfactants can damage the barrier layer of the skin. For this reason, neither emulsifiers nor surfactants are added to the preparations, i.e. the addition of additional washing-active substances is advantageously dispensed with.

Advantageously, skin-wetting agents, moisturizers, are added as active ingredient to the preparations.

The preparations are used on wet skin and in particular also for shaving.

The preparation according to the invention can be used for conditioning the skin.

It permits the generation of a skin protective film following application of the preparation to the skin and subsequent rinsing with water.

The protective film which is formed is ideally at least 1 µm thick (measured according to IR-ATR measurement technique) and/or comprises no substances that are harmful to the skin barrier, in particular no emulsifiers, surfactants, PEGs and/or organohalogen compounds.

Preferred embodiments of the preparations according to the invention comprise one or more waxes, a hydrocarbon mixture and an active ingredient from the group of the skin-wetting agents, where the fatty alcohols selected are myristyl, cetearyl and/or stearyl alcohols, the wax selected is Cera Microcristallina and the hydrocarbon mixture selected is Paraffinum Liquidum.

The skin-wetting active ingredient to be selected advantageously in this preparation is glycerol, as well as ubiquinone active ingredient Q10 for skincare and a cooling active ingredient such as menthol.

This three-way combination of active ingredients brings about a pleasant skin feel and care both during showering and also a long-lasting skincare.

As a neutralizing agent, sodium hydroxide is preferably present.

In the event of limitations to substances specified as preferred, be they lipids, waxes, active ingredients or film formers or further constituents specified as being preferred, then their preferred fraction ranges thus also refer to the individual constituents then selected. The other constituents excluded by the limitation then no longer count towards the listed fraction ranges.

DETAILED DESCRIPTION OF EMBODIMENTS

The examples below illustrate the preparation according to the invention in order to obtain preparations according to the invention.

The numerical values are fractions by weight, based on the total mass of the preparation.

| Ingredient | 1 | 2 | 3 | 4 | 5 |
|---|---|---|---|---|---|
| Cera Microcristallina | 25.000 | 16.5000 | 16.5000 | 35.000 | 45.000 |
| Paraffinum Liquidum | | 8.5000 | 8.5000 | | |
| Myristyl alcohol | 1.0000 | 1.0000 | 1.0000 | 2.0000 | |
| Cetearyl alcohol | 5.0000 | 5.0000 | 5.0000 | 4.0000 | 4.0000 |
| Stearyl alcohol | 2.0000 | 2.0000 | 2.0000 | 3.0000 | 3.0000 |
| Hydrogenated coco glycerides | 3.0000 | 3.0000 | 3.0000 | 2.0000 | 2.0000 |
| Almond oil | | | 0.3500 | | 0.7000 |
| Aluminum starch octenyl succinate | 1.0000 | 1.0000 | 1.0000 | 1.0000 | 1.0000 |
| Perfume | 0.8000 | 0.7000 | 1.0000 | 0.7000 | 0.7000 |
| Glycerol | 5.1000 | 5.1000 | 5.1000 | 15.100 | 10.100 |
| Sodium hydroxide solution 45% strength | 0.1600 | 0.1600 | 0.1600 | 0.1600 | 0.1600 |
| Phenoxyethanol | 0.5000 | 0.5000 | 0.5000 | 0.4000 | 0.4000 |
| Methylisothiazolinones | 0.0900 | 0.0900 | 0.0900 | 0.0800 | 0.0800 |
| Acrylates/C10-30 alkyl acrylate crosspolymer (Carbopol 3128) | 0.1000 | 0.1000 | 0.1000 | 0.1200 | |
| Carbomer (Carbopol 981) | 0.0200 | 0.0200 | 0.0200 | 0.0200 | 0.0200 |
| Acrylates/C10-30 alkyl acrylate crosspolymer (Pemulen TR-1) | 0.1000 | 0.1000 | 0.1000 | 0.1200 | 0.1400 |
| Sea salt | 0.0100 | 0.0100 | | 0.0100 | 0.0500 |
| Q10 | 0.0100 | 0.0050 | 0.0300 | 0.005 | 0.0010 |
| 4-Butylresorcinol | 0.3000 | 0.0010 | 0.1000 | | 0.0200 |
| N-(4-(2,4-Dihydroxyphenyl)-thiazol-2-yl)isobutyramide | 0.1000 | | 0.0250 | 0.0100 | |
| Creatine | 0.5000 | 1.0000 | | 0.0010 | |
| Niacinamide | 0.2000 | | 0.0010 | | 0.1000 |
| *Magnolia Officinalis* bark extract | 0.5000 | 0.1500 | | 0.2500 | |
| *Arctium Lappa* fruit extract | 0.1000 | 0.5000 | | | 0.0100 |
| *Glycyrrhiza Inflata* root extract | 0.0010 | | 0.0250 | | 0.1000 |
| 1,3-Dihydroxyacetone | 0.1500 | 1.0000 | 3.5000 | 0.8000 | 2.000 |
| Glyceryl glucoside | 5.0000 | 0.1000 | 1.5000 | | 0.0100 |
| Menthoxypropanediol | 0.1000 | 1.5000 | 0.6000 | 0.2000 | 0.0100 |
| Panthenol | | | 0.0100 | | |
| *Glycine soya* germ extract | | 0.2000 | | | 0.0500 |
| Glycyrrhetic acid | 0.0100 | | 0.1000 | 0.0050 | |
| Water | ad 100 | ad 100 | ad 100 | ad 100 | ad 100 |

| | 6 | 7 | 8 | 9 | 10 |
|---|---|---|---|---|---|
| Myristyl alcohol | | 1.00 | 1.00 | 1.00 | 1.00 |
| Cetearyl alcohol | 1.00 | 1.00 | 1.00 | 5.00 | 1.00 |
| Stearyl alcohol | 2.00 | | 2.00 | 2.00 | 2.00 |
| Hydrogenated coco glyceride | 3.00 | 3.00 | 3.00 | 3.00 | |
| Cera Microcristallina | 7.24 | 5.00 | | 16.50 | |
| Paraffinum Liquidum | | 2.04 | | 8.50 | |
| Paraffin | | | 7.24 | | 5.00 |
| Aluminum starch octenyl succinate + aqua | 1.00 | 1.00 | 1.00 | 1.00 | 1.00 |
| Perfume | 1.00 | 1.00 | 1.00 | 0.80 | 1.00 |
| Glycerine + aqua | 0.90 | 0.90 | 0.90 | 5.1 | 0.90 |
| Aqua + sodium hydroxide | 0.16 | 0.16 | 0.16 | 0.16 | 0.16 |
| Phenoxyethanol | 0.80 | 0.80 | 0.80 | 0.80 | 0.80 |
| Ethylparaben | | 0.10 | | | 0.10 |
| Methylparaben | | 0.30 | | | 0.30 |
| Acrylates/C10-30 alkyl acrylate crosspolymer | 0.10 | 0.10 | 0.10 | 0.10 | 0.10 |
| Carbomer | 0.02 | 0.02 | 0.02 | 0.02 | 0.02 |
| Acrylates/C10-30 alkyl acrylate crosspolymer | 0.10 | 0.10 | 0.10 | 0.10 | 0.10 |
| Trisodium EDTA | 0.10 | 0.10 | 0.10 | | 0.10 |
| Q10 | 0.01 | 0.005 | 0.03 | 0.0045 | 0.005 |
| 4-Butylresorcinol | 0.30 | 0.001 | 0.10 | | |
| N-(4-(2,4-Dihydroxyphenyl)-thiazol-2-yl)isobutyramide | 0.10 | | 0.025 | | 0.01 |
| Creatine | 0.50 | 1.00 | | | 0.001 |
| Niacinamide | 0.20 | | 0.001 | | |
| Menthol | | | | 0.30 | |
| Aqua | ad 100 | ad 100 | ad 100 | ad 100 | ad 100 |

What is claimed is:

1. A cosmetic or dermatological preparation, wherein the preparation is rinseable and emulsifier-free and comprises (i) one or more polyacrylic acid polymers, (ii) one or more C14-22 fatty alcohols, (iii) one or more waxes and/or a hydrocarbon mixture, and (iv) one or more active ingredients selected from warming substances, and wherein after rinsing the preparation leaves behind a film on skin to which it has been applied.

* * * * *